United States Patent [19]

Mackie

[11] Patent Number: 5,820,567
[45] Date of Patent: Oct. 13, 1998

[54] HEART RATE SENSING APPARATUS ADAPTED FOR CHEST OR EARLOBE MOUNTED SENSOR

[75] Inventor: Ronald David Lessels Mackie, Edinburgh, United Kingdom

[73] Assignee: Healthcare Technology Limited, West Susses, United Kingdom

[21] Appl. No.: 741,965

[22] Filed: Oct. 31, 1996

[30] Foreign Application Priority Data

Nov. 2, 1995 [GB] United Kingdom .................... 9522446

[51] Int. Cl.$^6$ ........................................................ A61B 5/02
[52] U.S. Cl. .......................... 600/519; 600/520; 600/509; 128/903
[58] Field of Search ...................................... 128/706, 707, 128/677, 696, 903; 601/35, 36; 600/490, 508, 509, 519, 520

[56] References Cited

U.S. PATENT DOCUMENTS

| 5,027,303 | 6/1991 | Witte ........................................ 364/511 |
|---|---|---|
| 5,335,664 | 8/1994 | Nagashima . |
| 5,417,221 | 5/1995 | Sickler ..................................... 128/696 |
| 5,456,262 | 10/1995 | Birnbaum ................................ 128/707 |
| 5,462,504 | 10/1995 | Trulaske et al. ......................... 128/707 |
| 5,464,021 | 11/1995 | Birnbaum ................................ 128/903 |
| 5,640,965 | 6/1997 | Maeyama . |
| 5,657,514 | 8/1997 | Fabrizio .................................. 128/696 |

*Primary Examiner*—William E. Kamm
*Assistant Examiner*—Carl H. Layno
*Attorney, Agent, or Firm*—Ira S. Dorman

[57] ABSTRACT

A heart rate sensing apparatus includes user mounted means for sensing the electrical activity of a user's heart and for transmitting a signal derived from the electrical activity of the user's heart. At least the sensing means can be mounted on the chest of the user. Signal receiving and processing means is provided, independent of the user mounted means, for receiving a signal transmitted from the user mounted means and for processing the shape of each signal so as to simulate an earlobe mounted sensor.

14 Claims, 3 Drawing Sheets

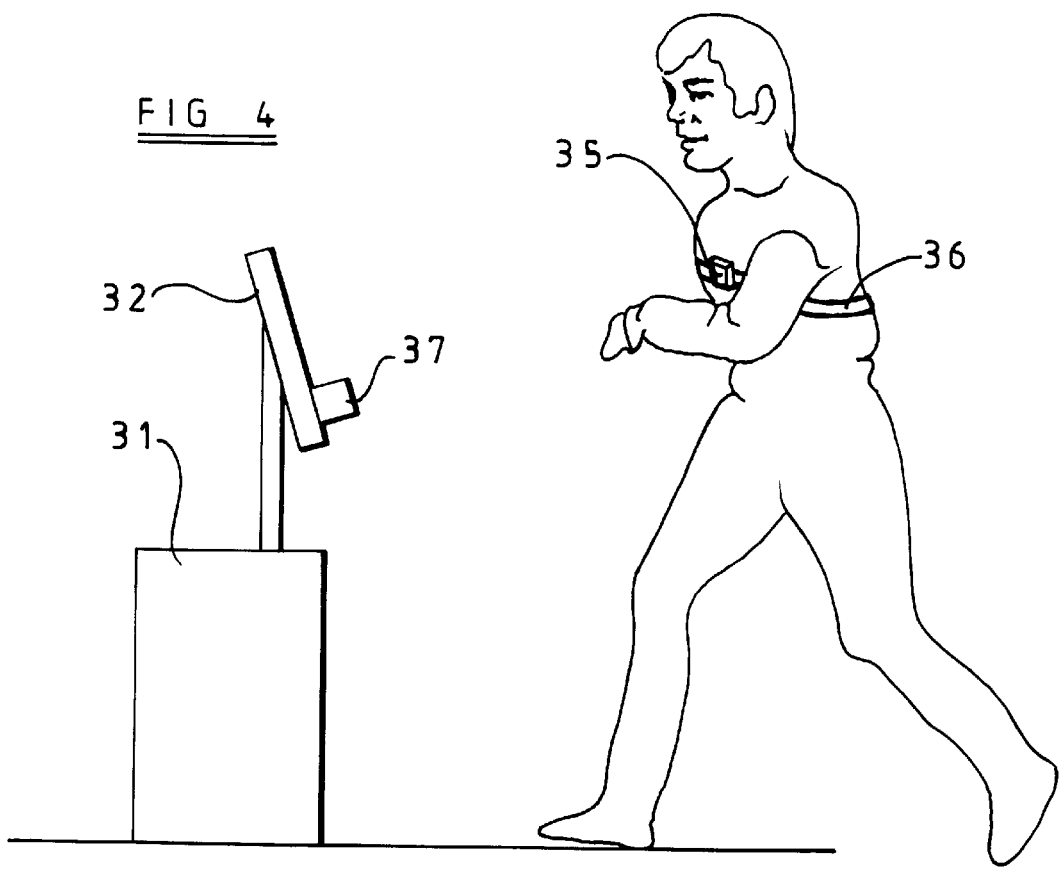
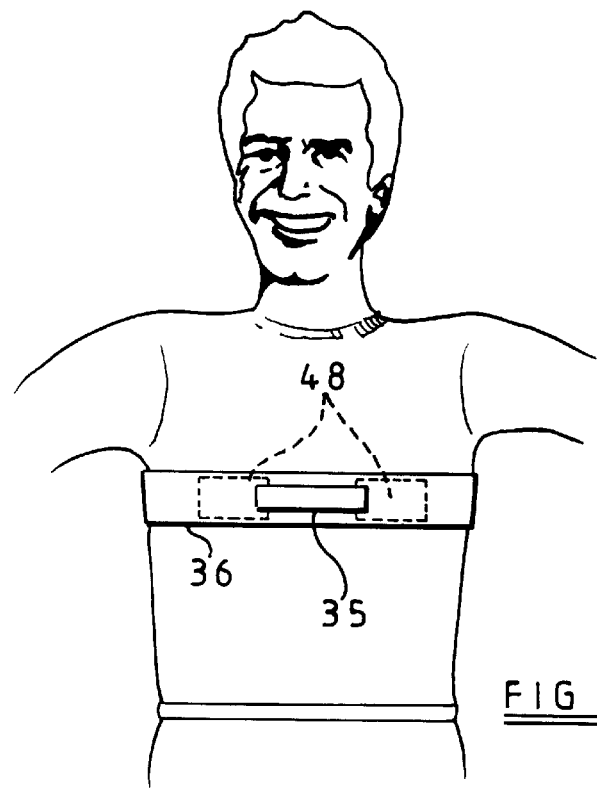

HEART RATE SENSING APPARATUS ADAPTED FOR CHEST OR EARLOBE MOUNTED SENSOR

The present invention relates to a heart rate sensing apparatus, for example for use as part of monitoring apparatus for measuring and reporting the heart rate of a person. The heart rate sensing apparatus according to the invention is particularly adapted to replace the earlobe sensing arrangement in heart rate monitors designed for use with earlobe sensors.

DESCRIPTION OF PRIOR ART

Many heart rate monitors, especially those mounted on exercise equipment, monitor the activity of the heart by sensing pulsating blood flow in an earlobe of an exercising person. Such a heart rate monitor and its sensing apparatus are shown in FIGS. 1 and 2 of the accompanying drawings.

Each heart beat sends a blood pressure wave through the vascular system and therefore the volume of blood present at a peripheral site on the body, such as an earlobe 15, varies periodically at a rate corresponding to the heart rate. Sensing of the blood pressure wave, and therefore of the heart rate, is commonly accomplished by directing a beam of infra-red radiation from a suitable infra-red emitting diode (LED) 16 through the earlobe 15 and detecting the transmitted beam with a photodiode or phototransistor 17 sensitive to infra-red radiation. Blood absorbs infra-red radiation and therefore the intensity of the detected transmitted beam is reduced when a greater than average volume of blood is present in the earlobe.

The electrical signal from the photodiode or photo transistor 17 therefore has a periodic component which fluctuates in accordance with the heart rate. This periodic component can be amplified until it has an amplitude sufficiently large to trigger circuitry which determines, or times, the beat-to-beat intervals. These timed intervals can then be converted to heart rate by electronic processing means, such as a microprocessor, and reported in the form of a display.

With particular reference to FIG. 2 of the accompanying drawings, the sensing means 13 is usually incorporated into a spring-biased clip 3 which grips the earlobe. The clip is provided with a connecting cable 4 which terminates in a plug 5 which, in turn, is inserted into a matching socket in a console 2 provided as part of the exercise equipment 1.

For a wide range of exercise equipment which uses this method of heart rate monitoring, the connecting cable 4 generally incorporates three conductors which are each connected to one of the three contacts of a 3.5 mm stereo jack plug. In practice, the ground line is connected to the shank 10 of the plug, the LED pulse line is connected to the tip 12, and the output signal from the photo transistor is connected to the mid-pole 11 of the plug. The sensing means is therefore removable from the console and moreover is easily replaced when damaged.

A typical voltage signal 20 from the phototransistor 17, after amplification in a preamplifier, is shown in FIG. 3. As can be seen from FIG. 3, the signal 20 exhibits a relatively slow rise 21 with the time between points A and B in FIG. 3 being typically 100 ms. The time from A to C in FIG. 3 represents the beat-to-beat interval and ranges from about 0.25 seconds for a heart rate of 240 beats per minute (bpm) to about 1.5 seconds for a heart rate of 40 bpm.

Earlobe sensors are commonly driven electronically by pulsing the infra-red LED periodically with high current for a short duration (known as positive-going pulses). This is done to reduce average current consumption while taking advantage of the characteristic of LEDs that they are more efficient at higher current.

Despite the ability to remove the sensing means from the console and to replace the sensing means when damaged, the use of an earlobe sensor connected to the console does have a number of disadvantages. For example:

1. the cable connecting the sensor to the console can restrict the user's freedom of movement;
2. it can be difficult to clip the sensor to the earlobe in a manner such that the sensor remains in position during strenuous exercise; and
3. in a cold environment there can be insufficient flow of blood in an earlobe due to contraction of the capillary blood vessels with the result that the amplitude of the detected periodic component may not be large enough to trigger the circuitry for determining the beat-to-beat intervals.

OBJECT OF THE INVENTION

It is therefore an object of the present invention to provide a heart rate sensing apparatus, for use with heart rate monitors adapted for earlobe sensing, which eliminates, or at least reduces, the above mentioned disadvantages and which provides a reliable and accurate measurement of heart rate even during strenuous exercise and in cold environments without restricting the user's freedom of movement.

SUMMARY OF THE INVENTION

According to the present invention there is provided a heart rate sensing apparatus comprising:

user mounted means for sensing the electrical activity of a user's heart and for transmitting a signal derived from the electrical activity of the user's heart, at least the sensing means being adapted to be mounted on the chest of the user; and signal receiving and processing means independent of the user mounted means for receiving a signal transmitted from the user mounted means and for processing the or each signal so as to simulate an earlobe mounted sensor.

The signal processing means may comprise means for generating a pulse in response to a heart beat and means for shaping the edges of the pulse. The means for generating a pulse may comprise a monostable circuit. The means for shaping the edges of the pulse are preferably adapted to shape the edges of the pulse with a time constant of about 100 milliseconds. The means for shaping the edges of the pulse may comprise a resistor in series with the signal and a capacitor in parallel with the signal. The signal processing means may include means for limiting the magnitude of the signal current.

A power supply for the signal processing means and/or the receiver may be derived from drive pulses generated by the heart rate monitor and intended for driving an infra-red LED) of an earlobe sensor. The power supply may comprise a diode and a storage capacitor. The diode preferably comprises a Schottky diode.

The transmitter and the receiver may comprise a radio transmitter and receiver operating, for example, at 5 kHz. Alternatively, the transmitter and the receiver may comprise an infra-red transmitter and receiver.

For a better understanding of the present invention and to show more clearly how it may be carried into effect reference will now be made, by way of example, to the accompanying drawings in which:

BRIEF DESCRIPTION OF THE DRAWINGS

FIG. 4 is a diagrammatic illustration of a heart rate monitoring system employing a heart rate sensing apparatus according to the present invention;

FIG. 5 is a diagrammatic view of a user wearing part of a heart rate sensing apparatus according to the present invention;

DESCRIPTION OF PREFERRED EMBODIMENTS

Figure 1:
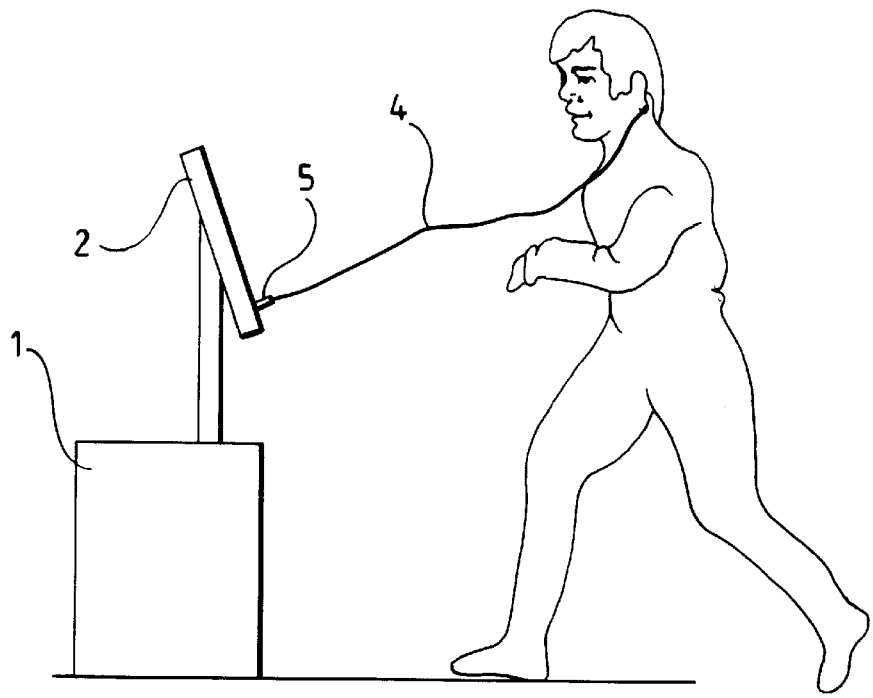
FIG. 1 is a diagrammatic illustration of a known heart rate monitoring system using an earlobe sensor.
Figure 2:
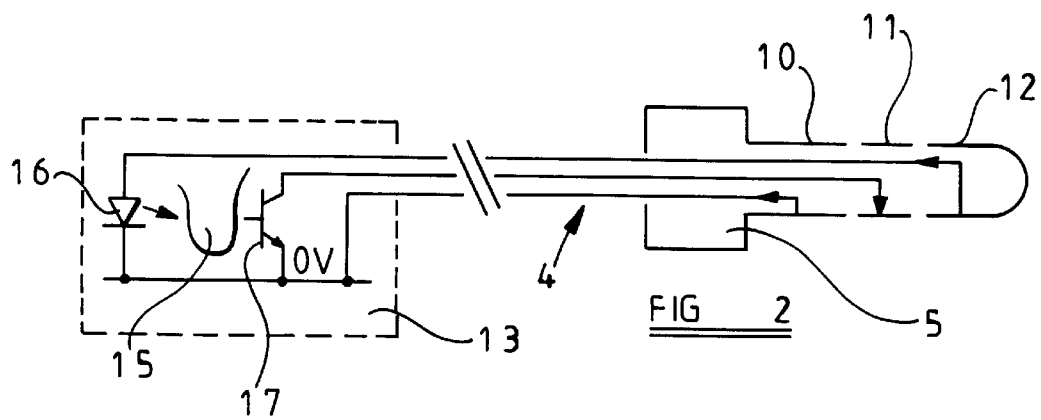
FIG. 2 is a diagrammatic illustration of the electronic components of an earlobe sensor, connecting cable and associated plug for use in the known heart rate monitoring system of FIG. 1.
Figure 3:
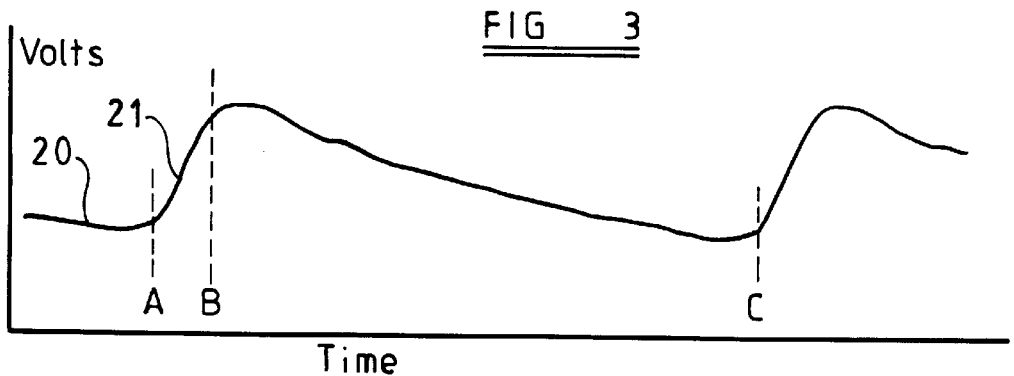
FIG. 3 is a graphical representation of a typical electrical signal produced by the preamplifier of a known earlobe sensor.

In order to replace the earlobe sensor with an alternative sensor, while maintaining compatibility with existing heart rate monitors designed for earlobe sensors, any alternative sensor must be able to:

1. extract sufficient current at a suitable voltage from the LED drive pulses to operate the electrical components of the alternative sensor; and
2. generate a signal which simulates the signal that would have been produced by an earlobe sensor.

With regard to the first requirement, it is clear that any alternative sensor must have very low current consumption and be able to operate at low voltage. With regard to the second requirement, it is also necessary to bear in mind that any alternative sensor must generate a signal that is compatible with a range of heart rate monitors designed to operate in conjunction with earlobe sensors.

In the embodiment of the present invention illustrated in FIGS. 4 to 8, the known earlobe sensor is replaced by a sensing and transmitting module 35 and by a receiving module 37 which is plugged into the console 32 of exercise equipment 31. As shown in FIGS. 4 and 5, the sensing and transmitting module 35 is mounted on a chest belt 36 which, in use, is worn by the user. As shown in FIG. 5, conducting rubber or like contacts 48 make electrical connection with the skin of the user in order to pick up the electrical signal, in particular each R-wave in the user's ECG signal, from the user's heart in known manner and to convey the signal to an amplifier within the module 35.

Figure 6:
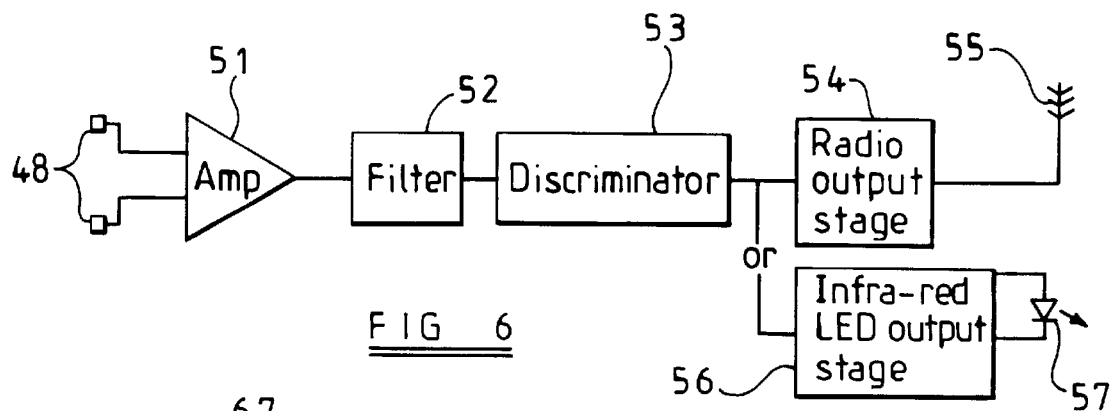
FIG. 6 is a block diagram of electronic circuitry contained within the chest-worn transmitter illustrated in FIG. 5.

The electronic components within the chest-worn module 35 are shown diagrammatically in FIG. 6. As can be seen from FIG. 6, an amplifier 51 amplifies the signal from the two contacts 48. Extraneous high and low frequencies are removed by filter circuit 52 and, when the resulting signal attains a sufficient amplitude, discriminator circuit 53 triggers an output stage which may comprise, for example, either a radio transmitter 54 with an aerial 55 or an infra-red transmitter 56 with an output LED 57. Typically, the output consists of either a 10 ms burst of 5 kHz radio waves or a 50 microsecond flash of infra-red radiation.

Figure 7:
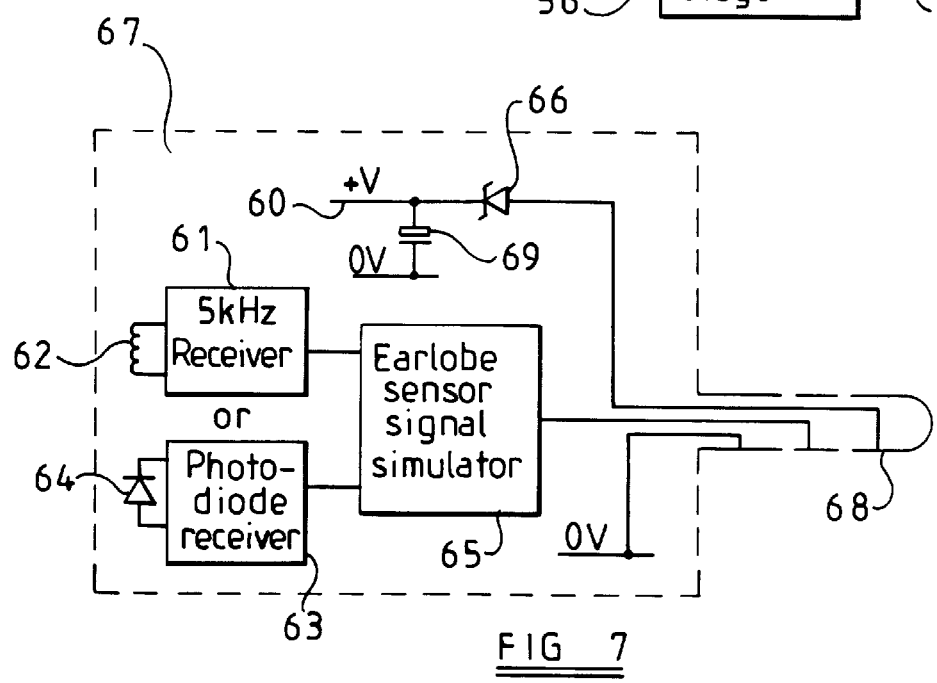
FIG. 7 is a block diagram of electronic circuitry contained within a plug-in module.

FIG. 7 diagrammatically illustrates a plug-in module 67 to replace the plug of an earlobe sensor. The function of the module 67 is to receive heart beat signals from the chest-worn transmitter 35 and to convert each received signal into a signal which triggers the electronics of the console of the exercise equipment as though the signal originated from an earlobe sensor.

Depending on the nature of the transmitter 35, the module 67 incorporates either a radio receiver 61 for receiving the 5 kHz waves from the transmitter by way of an aerial coil 62 or infra-red receiver circuitry 63 for receiving infra-red radiation from the transmitting LED by way of a photodiode receiver 64. The signals from the radio or infra-red receiver are passed to circuitry 65 which generates a signal simulating an earlobe sensor signal and which will be described in more detail hereinafter.

A power supply 60 for energizing the circuitry 65 and, if necessary, the receiver 61 or 63 is generated by rectifying the LED drive pulses from the console of the exercise equipment with a diode 66 and storage capacitor 69. To minimise the voltage drop across diode 66, the diode should be in the form of a Schottky diode.

Electrical connections between the electronic components and a jack plug 68 correspond to the common wiring convention for earlobe sensors in order that the module 67 can be substituted for the plug of an earlobe sensor.

Figure 8:
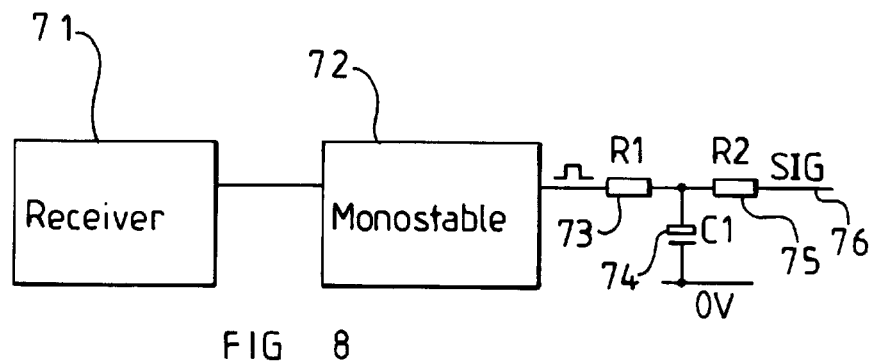
FIG. 8 is a block diagram in more detail of part of the electronic circuitry shown in FIG. 7.
Figure 1:
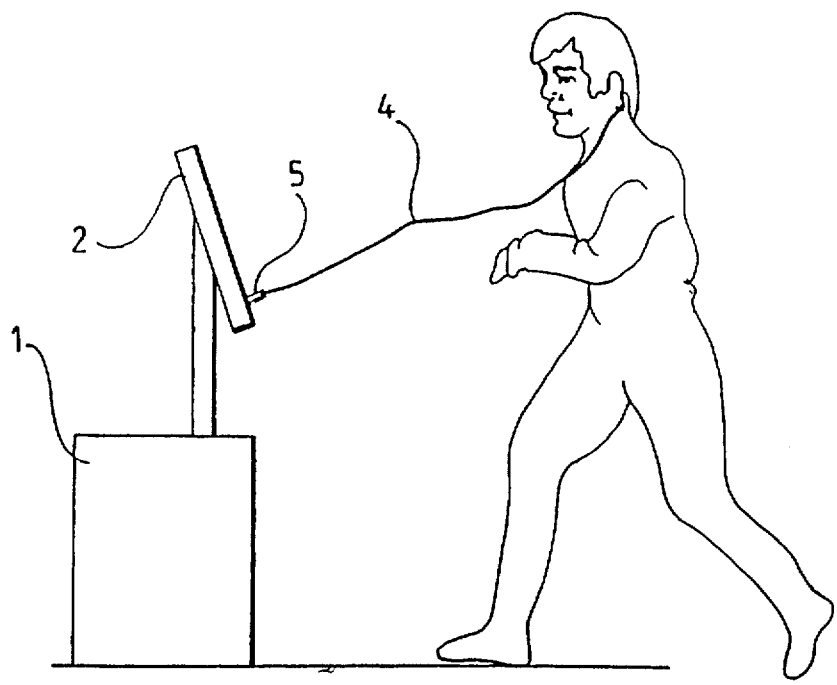
Figure 2:
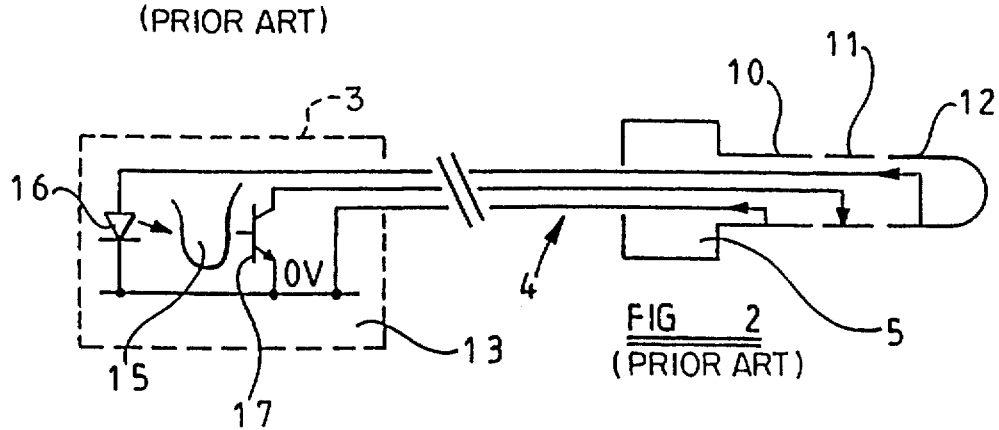
Figure 3:
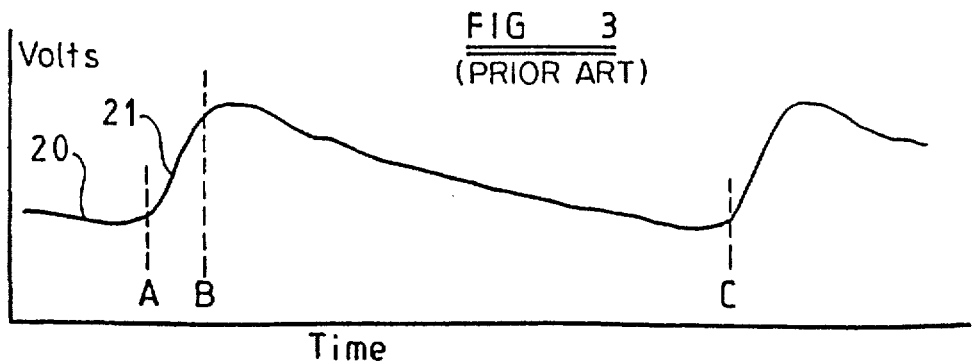
Figure 6:
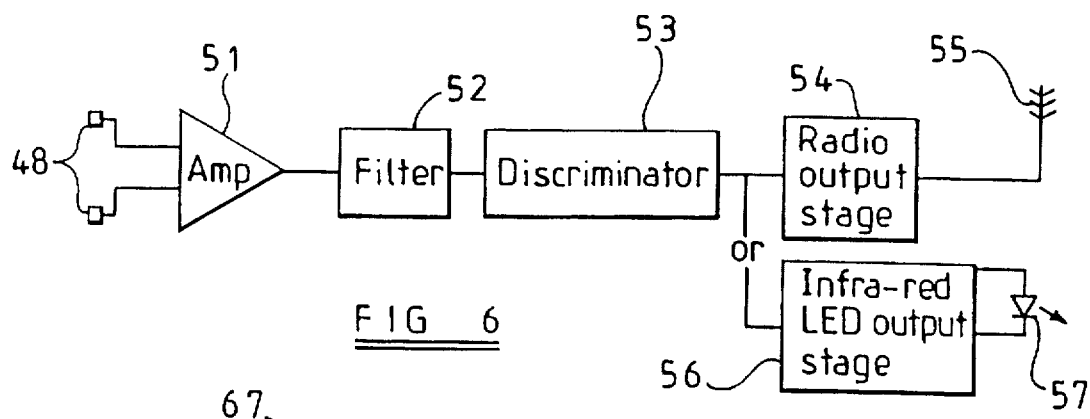
Figure 7:
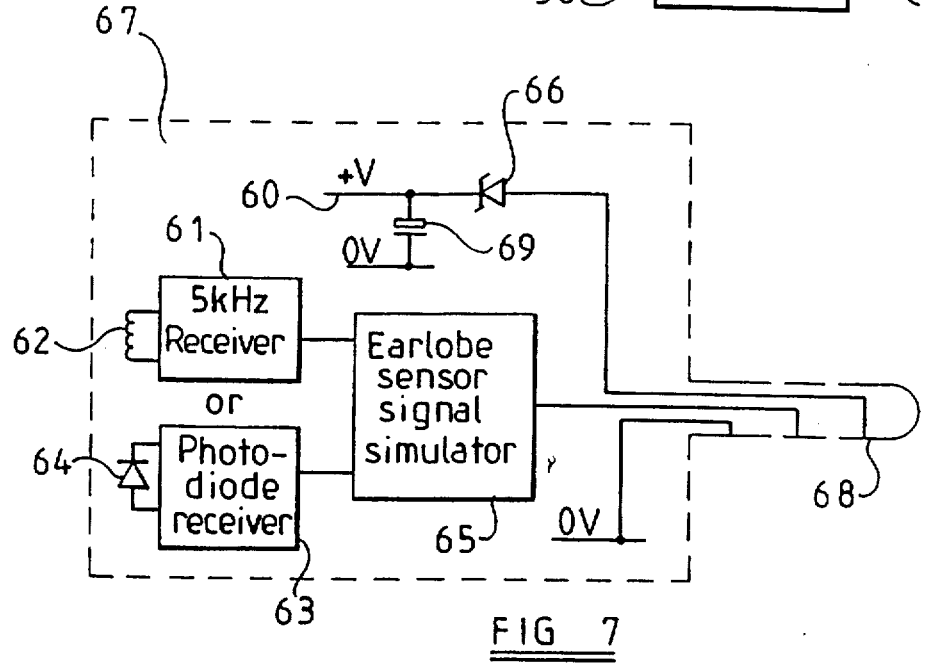
Figure 8:
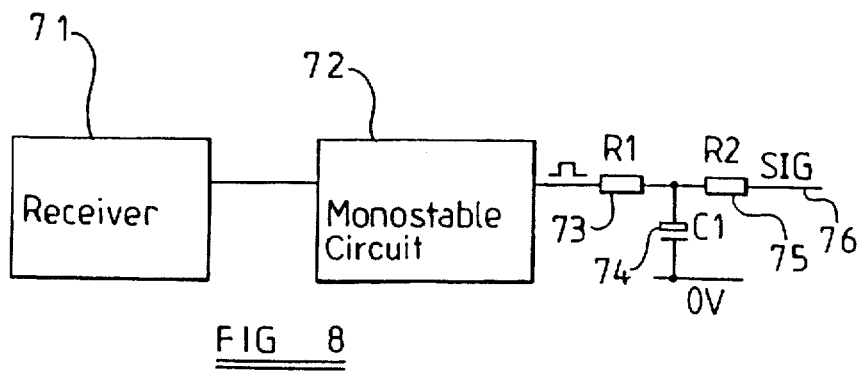

Typical shaping circuitry is shown in FIG. 8 in which the output from a receiver 71, such as radio receiver 61 or infra-red receiver 63, is standardised into a positive-going pulse of fixed duration by a monostable circuit 72. Resistor 73 and capacitor 74 shape the edges of the pulse with a time constant of about 100 ms to simulate the rise time of an earlobe pulse. In order to match the signal current supplied from an earlobe sensor, resistor 75 controls the magnitude of the signal current fed to the console electronics by way of a line 76 to the jack plug 68.

Compared with an earlobe sensor, the advantages of the present invention as described with reference to FIGS. 4 to 8 of the accompanying drawings are:

1. no cable connecting the user to the monitoring equipment and therefore the mobility of the user is not constrained;
2. the heart signal sensor on the chest of the user is more firmly held in place than is an earlobe sensor and therefore there is less likelihood of sensor signal loss;
3. heart signal sensing is adequate even in low ambient temperatures; and
4. no modification of existing monitoring equipment is necessary in order to replace an earlobe sensor with a sensing apparatus according to the invention.

I claim:

1. A heart rate sensing apparatus comprising:

user mounted means for sensing electrical activity of a user's heart and for transmitting a signal derived from the electrical activity of the user's heart, at least the sensing means being adapted to be mounted on a chest of the user; and signal receiving and processing means independent of the user mounted means for receiving at least one signal transmitted from the user mounted means and for processing each signal so as to simulate an earlobe mounted sensor, the signal receiving and processing means incorporating plug means adapted for removably mounting the signal receiving and processing means in equipment adapted to process signals emitted by an earlobe sensor.

2. A heart rate sensing apparatus according to claim 1, wherein the signal processing means includes means for limiting the magnitude of the signal current.

3. A heart rate sensing apparatus according to claim 1, wherein the user mounted means comprises an infra-red transmitter and the signal processing means comprises an infra-red receiver.

4. A heart rate sensing apparatus according to claim 1, wherein the user mounted means comprises a radio transmitter and the signal processing means comprises a radio receiver.

5. A heart rate sensing apparatus according to claim 4, wherein the transmitter and receiver incorporate means for transmitting and receiving signals at 5 kHz.

6. A heart rate sensing apparatus comprising:

user mounted means for sensing electrical activity of a user's heart and for transmitting a signal derived from the electrical activity of the user's heart, at least the sensing means being adapted to be mounted on the chest of the user; and signal receiving and processing means independent of the user mounted means for receiving at least one signal transmitted from the user mounted means and for processing each signal so as to simulate an earlobe mounted sensor, the signal processing means comprising means for generating a pulse in response to a heart beat and means for shaping edges of the pulse.

7. A heart rate sensing apparatus according to claim 6, wherein the means for generating a pulse comprises a monostable circuit.

8. A heart rate sensing apparatus according to claim 6, wherein the means for shaping the edges of the pulse are adapted to shape the edges of the pulse with a time constant of about 100 milliseconds.

9. A heart rate sensing apparatus according to claim 6, wherein the means for shaping the edges of the pulse comprises a resistor in series with the signal and a capacitor in parallel with the signal.

10. A heart rate sensing apparatus according to claim 6, wherein the signal processing means includes means for limiting the magnitude of the signal current.

11. A heart rate sensing apparatus comprising:

user mounted means for sensing electrical activity of a user's heart and for transmitting a signal derived from the electrical activity of the user's heart, at least the sensing means being adapted to be mounted on the chest of the user;

signal receiving and processing means independent of the user mounted means for receiving at least one signal transmitted from the user mounted means and for processing each signal so as to simulate an earlobe mounted sensor; and a power supply means for at least one of the signal processing means and the receiver, deriving a power supply output from drive pulses generated by the sensing means and intended for driving an infra-red LED of an earlobe sensor.

12. A heart rate sensing apparatus according to claim 11, wherein the power supply comprises a diode connected in series with the drive pulses and a storage capacitor connected in parallel with the drive pulses.

13. A heart rate sensing apparatus according to claim 12, wherein the diode comprises a Schottky diode.

14. A heart rate sensing apparatus comprising:

user mounted means for sensing electrical activity of a user's heart and for transmitting a signal derived from the electrical activity of the user's heart, at least the sensing means being adapted to be mounted on the chest of the user;

signal receiving and processing means independent of the user mounted means for receiving at least one signal transmitted from the user mounted means and for processing each signal so as to simulate an earlobe mounted sensor; and a power supply means for at least one of the signal processing means and the receiver, deriving a power supply output from drive pulses generated by the sensing means and intended for driving an infra-red LED of an earlobe sensor, the power supply means comprising a Schottky diode in series with the drive pulses and a storage capacitor in parallel with the drive pulses.

* * * * *

UNITED STATES PATENT AND TRADEMARK OFFICE
CERTIFICATE OF CORRECTION

PATENT NO.   : 5,820,567
DATED        : Oct. 13, 1998
INVENTOR(S)  : Makie

It is certified that error appears in the above-identified patent and that said Letters Patent is hereby corrected as shown below:

Please delete drawing sheets 1 of 3 & 3 of 3 and substitute drawing sheets 1 of 3 and 3 of 3 as per attached.

Signed and Sealed this

Twenty-third Day of March, 1999

Attest:

Q. TODD DICKINSON

Attesting Officer

Acting Commissioner of Patents and Trademarks